US006675468B2

(12) United States Patent
Benner

(10) Patent No.: US 6,675,468 B2
(45) Date of Patent: Jan. 13, 2004

(54) SYSTEM FOR ASSEMBLING DENTAL FLOSS DISPENSER COMPONENTS

(75) Inventor: Gary A. Benner, Metuchen, NJ (US)

(73) Assignee: Johnson & Johnson Consumer Products, Inc., Skillman, NJ (US)

( * ) Notice: Subject to any disclaimer, the term of this patent is extended or adjusted under 35 U.S.C. 154(b) by 0 days.

(21) Appl. No.: 10/094,262

(22) Filed: Mar. 8, 2002

(65) Prior Publication Data

US 2002/0088104 A1 Jul. 11, 2002

Related U.S. Application Data

(62) Division of application No. 08/527,671, filed on Sep. 13, 1995, now Pat. No. 6,357,102.

(51) Int. Cl.[7] .................................................. B23P 21/00
(52) U.S. Cl. .............................. 29/785; 29/792; 29/711
(58) Field of Search .......................... 29/785, 792, 806, 29/430, 791, 407.01, 711, 712, 714, 719, 790, 407.04; 53/252, 253

(56) References Cited

U.S. PATENT DOCUMENTS

| 2,092,786 | A | * | 9/1937 | Taylor | 29/785 |
|---|---|---|---|---|---|
| 3,466,731 | A | * | 9/1969 | Acton et al. | 29/785 |
| 3,802,051 | A | * | 4/1974 | Andler et al. | 29/806 |
| 3,802,052 | A | * | 4/1974 | Andler et al. | 29/806 |
| 3,840,966 | A | * | 10/1974 | Reid et al. | 29/785 |
| 4,441,955 | A | * | 4/1984 | Richardson et al. | 29/786 |
| 4,656,737 | A | * | 4/1987 | Shimizu et al. | 29/806 |
| 5,038,464 | A | * | 8/1991 | Suzuki et al. | 29/806 |
| 5,161,302 | A | * | 11/1992 | Mueller | 29/785 |
| 5,669,205 | A | * | 9/1997 | Rice et al. | 53/430 |
| 6,092,352 | A | * | 7/2000 | Tanaka | 29/806 |
| 6,128,885 | A | * | 10/2000 | Karaki et al. | 29/806 |

* cited by examiner

Primary Examiner—David P. Bryant

(57) ABSTRACT

A system including an apparatus and method for assembling an insert and a cutter bar into a subassembly for use in dental floss dispensers. The insert includes a body portion defining an arbor for rotatably supporting a spool of dental floss and a superstructure contiguous with the body portion. The superstructure includes cutter bar receiving structure adapted to be grippingly engaged by a cutter bar having a cutting blade portion. The apparatus includes a rotatable assembly wheel having multiple pockets for receiving inserts, which wheel is rotatable into a plurality of positions corresponding to a plurality of assembly stations. An insert is inserted into a wheel pocket in a first direction at a first assembly station, a cutter bar is pushed onto the insert's cutter bar receiving structure at a second assembly station and the subassembly is discharged in a direction opposite to the direction of insertion at a third assembly station. The apparatus preferably includes several sensing means for determining the status of the subassembly throughout the assembly procedure. The apparatus is preferably controlled by a computer such that a plurality of subassemblies may be simultaneously and synchronously assembled.

21 Claims, 4 Drawing Sheets

SYSTEM FOR ASSEMBLING DENTAL FLOSS DISPENSER COMPONENTS

CROSS REFERENCE TO RELATED APPLICATIONS

This is a divisional of application Ser. No. 08/527,671, filed Sep. 13, 1995, now U.S. Pat. No. 6,357,102.

FIELD OF THE INVENTION

The present invention relates in general to parts assembly systems and, more particularly, to systems including apparatus and methods of assembling component parts of dental floss dispensers.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes, threads and any similar article.

Dental floss is typically distributed in a compact dispenser from which a user may conveniently extract desired lengths of floss for dental cleansing purposes. The dispenser normally includes a dispenser case having a releasable lid. Typically enclosed within the dispenser case are an insert, a spool of dental floss rotatably supported by the insert, and a cutter bar carried by the insert. The free or "tail" end of the spool of floss is usually threaded through an eyelet provided in the insert near the top of the dispenser as well as the cutting blade portion of the cutter bar. In order to draw a length of floss from the dispenser, a user grasps the tail end of the floss and pulls until a desired length has been drawn, and then cuts the drawn length using the cutter bar. As the user pulls the floss from the dispenser, the spool rotates, thereby allowing the floss to be unwound from the spool.

In the manufacture of the various components of a conventional dental floss dispenser, experience has shown that, for purposes of economy and performance, the aforesaid insert should preferably be formed from molded plastic material whereas the cutter bar functions best when fabricated from stamped metal sheet. Metal is the material preferred for the cutter bar as it produces a cutting blade portion having a cutting edge sufficiently sharp to permit easy cutting of the dental floss. Being formed from such disparate materials, however, the cutting blade must be physically joined to the insert during a dispenser manufacturing process to produce a combined cutter bar and insert subassembly.

At present, at least two types of automated machinery have been developed to unite a dental floss dispenser cutter bar with its associated insert. According to a first design, two conveyors are employed to deliver separate streams of inserts and cutter bars to an assembly device. The insert conveyor serially transports the inserts side-by-side in a substantially horizontal orientation. As the leading insert reaches the assembly device it is urged laterally into an elongated channel. Once in the channel, it is pushed therealong by a push rod. At the completion of the push rod stroke, the insert is intended to abut a stop member at one end of the channel such that cutter bar receiving structure provided on the insert is exposed to receive a cutter bar. The leading cutter bar in a stream of serially arranged cutter bars delivered by the cutter bar conveyor is then press-fit onto the insert's cutter bar receiving structure by extension of a suitable linear operator means such as a pneumatic piston and cylinder assembly, or the like. Upon retraction of the linear operator means the united cutter bar and insert subassembly is supposed to fall from a discharge opening in the bottom of the channel and into a collection bin from which it may be recovered for assembly (along with a spool of dental floss) into a dispenser case.

It has been discovered, however, that gravity acting alone or with the slight assistance provided by the retraction of the linear operator means is frequently insufficient to positively dislodge the cutter bar/insert subassembly from the channel whereby it may fall through the channel discharge opening. Consequently, the entire cutter bar and insert assembly line must be brought to a halt and the jammed subassembly physically removed by the machine operator. Furthermore, the relatively long stroke of the push rod oftentimes causes the insert to become misaligned in its path of travel along the channel. In many instances such misalignment is serious enough to prevent a cutter bar from being placed onto the insert receiving structure. In addition, the machine may jam and damage may result to the cutter bar, the insert or both. In such case, production must again be stopped to free the jam. As will be appreciated, work stoppages of the types described result in considerable downtime, labor costs and waste part expenses.

An alternative approach has been to feed inserts substantially vertically into radially directed holding slots of a rotatable, horizontally disposed, multiple station assembly wheel. Cutter bars are press-fit laterally onto the inserts by cam-type operator means at another station of the assembly member. With such equipment, problems occasionally arise in connection with removal of the subassemblies from the assembly apparatus. In particular, the apparatus include means, typically in the form of radially disposed pistons carried by the assembly member for ejecting the inserts from the holding slots in a radial direction, i.e., substantially perpendicular to their direction of insertion into the holding slots. Additionally, the holding slots are fitted with means for laterally gripping opposite side edges of the inserts. So constructed, the gripping means tend to resist the radially directed expulsion forces exerted by the ejecting means. Such resistance is sometimes sufficient to prevent discharge of the subassemblies from their respective holding slots, thereby jamming the equipment and compressively damaging the inserts. In addition, the irregular shapes of such inserts many times causes the inserts to become misaligned with respect to the holding slots as the inserts are vertically fed into the slots. Mispositioning of the inserts, in turn, inhibits proper placement of the cutter bars onto the inserts. As a further drawback, the cam-type operator means presents the cutter bar at an angle with respect to the insert's cutter cutter bar receiving structure whereby the cutter bar is rotated about the receiving structure as it is pressed thereon. If any of the cutter bar and insert spatial and positioning criteria are not completely satisfied, attachment of the cutter bar to the insert will likely fail and either or both of the insert and cutter bar may be damaged. Hence, the assembly process must be stopped and jammed or damaged parts must be removed, resulting once again in the production inefficiencies discussed above.

An advantage exists, therefore, for an apparatus and method for assembling the insert and cutter bar of a dental floss dispenser in a continuous, synchronous and reliable operation which minimizes manufacturing disruptions and the attendant downtime and costs associated therewith.

SUMMARY OF THE INVENTION

The present invention provides a system including an apparatus and method for assembling dental floss dispenser subassemblies which include an insert and a cutter bar. The insert typically comprises a body portion defining an arbor adapted to rotatably support a spool or bobbin wound with a length of dental floss and a superstructure contiguous with the body portion, the superstructure including cutter bar receiving structure onto which the cutter bar is adapted to be attached. The typical cutter bar is generally C-shaped in cross-section including an upper leg in which is formed the cutting blade portion, a lower leg, and a web connecting the upper and lower legs. The upper and lower legs are adapted to grip the insert's cutter bar receiving structure when the cutter bar is installed thereon.

The instant apparatus includes a first conveyor for transporting inserts from a source of inserts to an assembly member. Likewise, the apparatus additionally comprises a second conveyor for transporting cutter bars from a source of cutter bars to the assembly member.

According to a presently preferred embodiment, the assembly member comprises a computer controlled, motor driven, rotatable wheel or disk having at least one or, more preferably, a plurality of holding slots or pockets adapted to securely yet gently receive inserts delivered from the first conveyor. During operation, the assembly member is indexed to a plurality of assembly stations. At a first assembly station the first conveyor delivers a leading insert into a holding pocket. From there, the motor indexes the rotatable wheel to a position where a first sensing device determines whether the insert has been properly inserted into the holding pocket. If an insert is properly inserted, the motor indexes the rotatable wheel to a second assembly station where a cutter bar may be placed onto the insert.

At the second assembly station the apparatus includes several strategically oriented components, namely, the discharge end of the second conveyor, stop means for aligning the leading cutter bar with the insert, and means for placing the cutter bar onto the insert. Upon the insert's arrival at this station, the cutter bar placement means is activated push the cutter bar into press-fitting engagement with the cutter bar receiving structure to establish the cutter bar/insert subassembly. The placement means is then retracted to a "ready" position.

Following this, the wheel is rotated by the motor to a position where a second sensing device determines whether the cutter bar is absent or mispositioned with respect to the cutter bar, i.e., whether the subassembly constitutes a "good" or a "bad" part. If it is determined that the subassembly is properly assembled, the computer commands the motor to index the wheel to a good part discharge site of a third assembly station. At this location means are provided to positively discharge the subassembly into a collecting bin for later placement along with a spool of dental floss into a dispenser case. If, however, the second sensing device determines that the subassembly is defective, the computer logic controls the motor to rotate the wheel to a bad or reject part discharge site of the third assembly station. At this location means are provided to positively discharge the defective subassembly into a reject part bin from which it may be further inspected and/or discarded.

The wheel is thereafter rotated to another position where there is located a third inspection device for determining if the subassembly, whether "good" or "bad," has been properly discharged from the wheel. If no part is detected, the wheel is rotated to a "home" station where calibration of the assembly member may be effectuated (which typically occurs before an assembly production run is begun).

Lastly, the wheel is rotated to the first assembly station where it may receive another insert from the leading end of the first conveyor whereby the assembly process is repeated. As noted above, it is preferred that the wheel be constructed with a plurality of holding pockets such that several subassemblies may be simultaneously assembled.

The structural arrangement of the instant apparatus and its method of operation affords gentle and precise handling and assembly of the cutter bar and insert. It does so in a continuous, synchronous and reliable manner which reduces the likelihood of part jams, thereby enhancing assembly productivity while reducing manufacturing costs.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments therefor shown, by way of example only, in the accompanying drawings, wherein.

DETAILED DESCRIPTION OF THE PREFERRED EMBODIMENT

Figure 1:
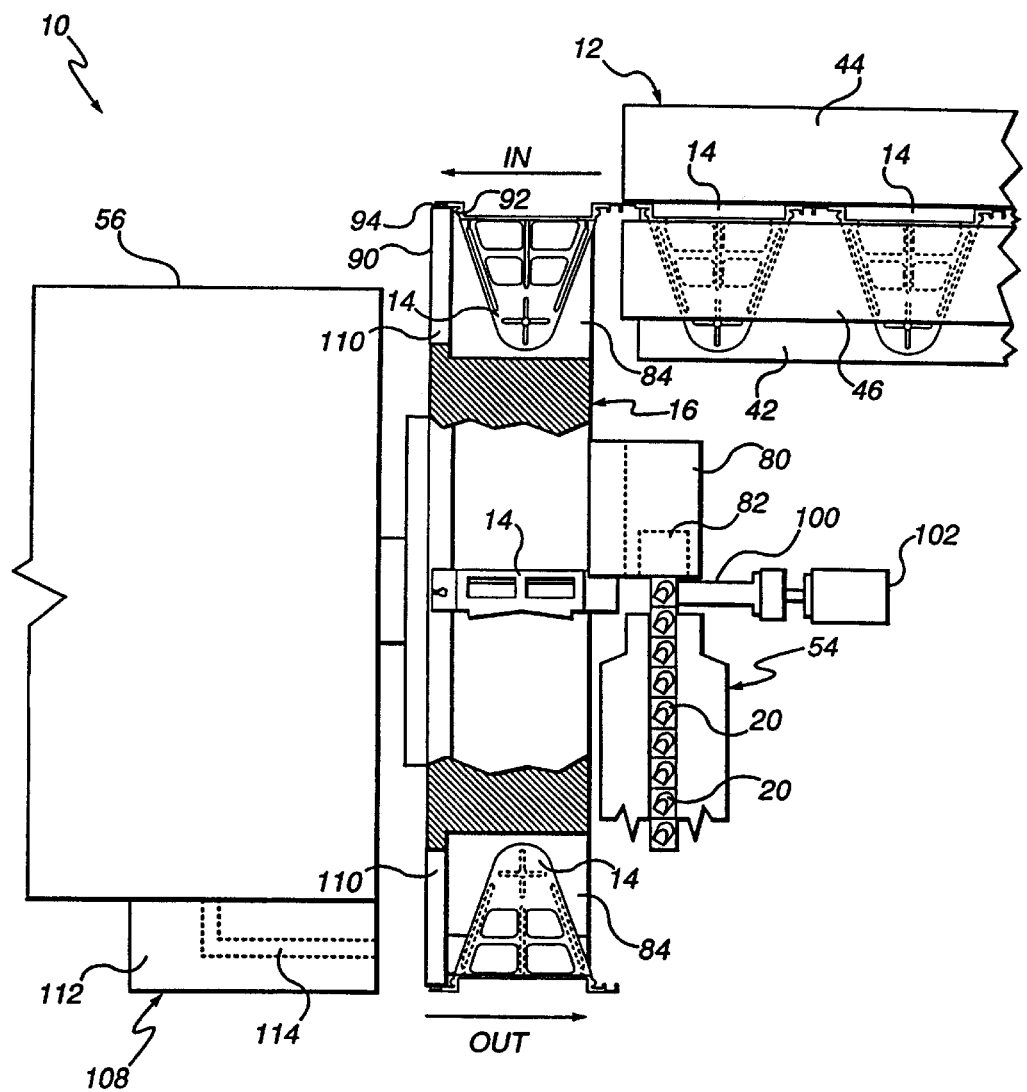
FIG. 1 is a top plan view, in partial section, partially cut away and with certain elements omitted for clarity, of a presently preferred embodiment of the cutter bar/insert assembly apparatus of the present invention.
Figure 2:
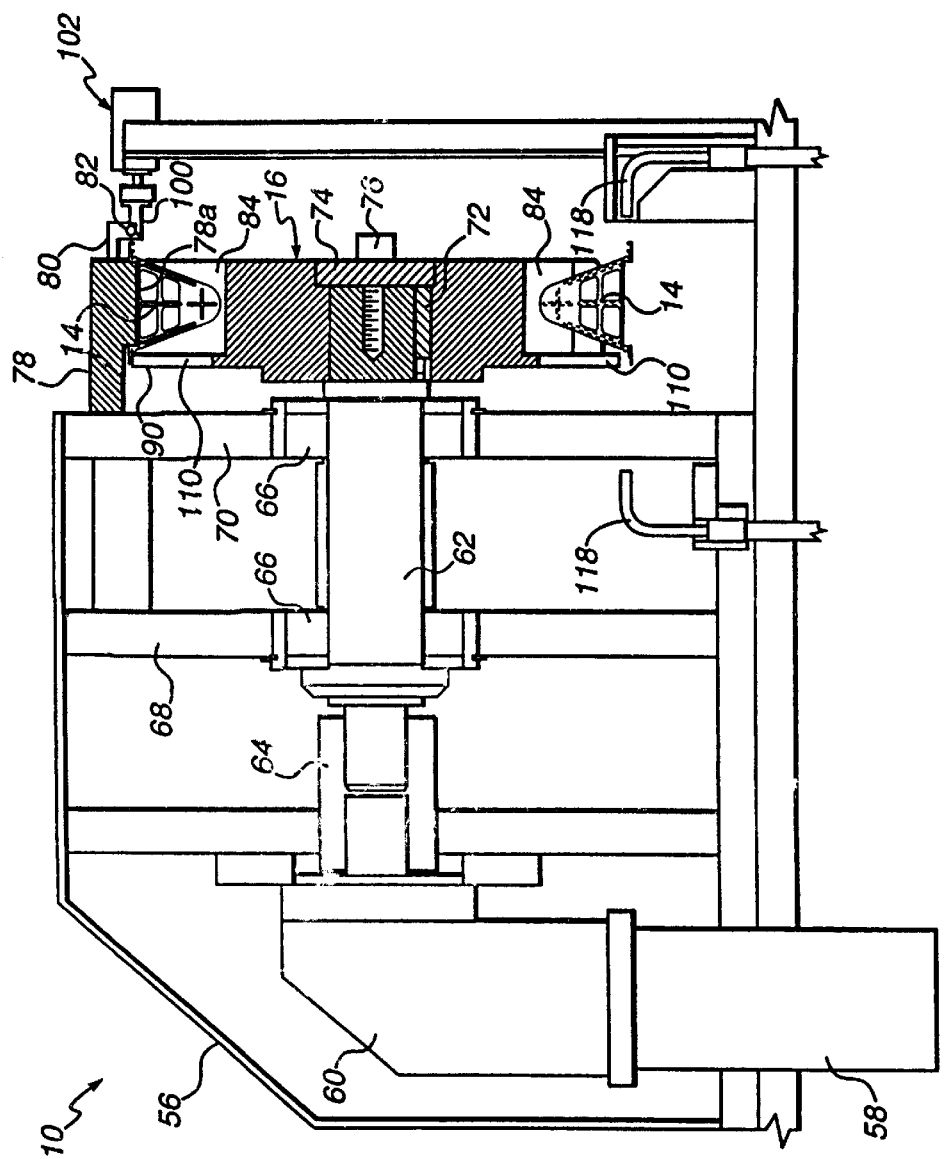
FIG. 2 is a side elevation view, in partial section and with certain elements omitted for clarity, of the cutter bar/insert assembly apparatus shown in FIG. 1.

Referring to FIGS. 1 and 2, there is shown an apparatus 10 according to the present invention for assembling dental floss dispenser components, in particular, cuter bar/insert subassemblies. Apparatus 10 includes a first conveyor 12 for transporting inserts 14 in side-by-side serial relation from an unillustrated source of inserts to a first assembly station of an assembly member 16, which assembly member is described in greater detail hereinafter.

Figure 4:
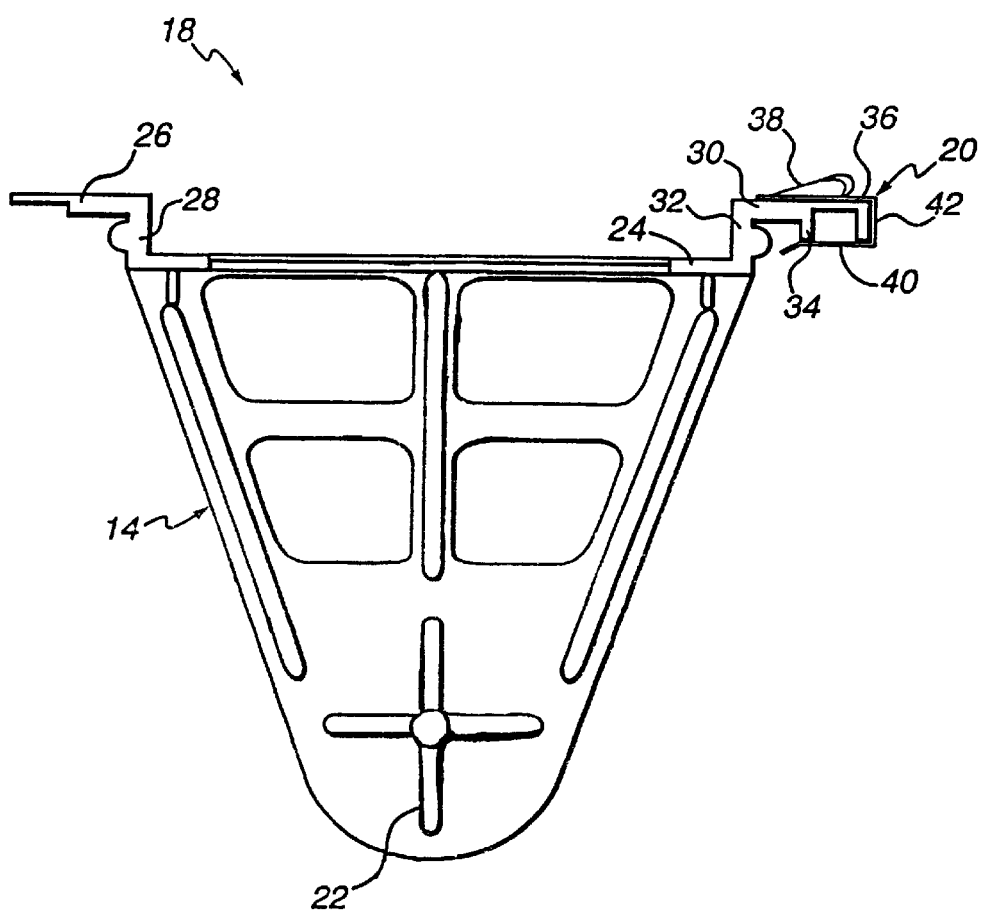
FIG. 4 is an enlarged view of a cutter bar/insert subassembly in assembled condition.

One such insert 14 is shown as being part of an assembled cutter bar/insert subassembly 18 depicted in FIG. 4 wherein the cutter bar thereof is identified by reference numeral 20. The insert 14 may be formed from any suitable material, although in commercial practice it is typically made from molded plastic material such as polypropylene, or the like. The insert generally includes a body portion defining an arbor 22 adapted to rotatably support an unillustrated spool or bobbin wound with a length of dental floss. Insert 14 further comprises a superstructure contiguous with the body portion which includes a platform 24, a first flange 26 joined to the platform by a first web 28 and a second flange 30 joined to the platform by a second web 32. The second flange 30 typically carries cutter bar receiving structure 34 which usually assumes the form of one or more downwardly depending projections.

Cutter bar 20 is normally formed from stamped metal, typically steel, sheet. The cutter bar is usually generally C-shaped in cross-section including an upper leg 36 in which is formed a cutting blade portion 38, a lower leg 40, and a web 42 connecting the upper and lower legs 36, 40. As FIG. 4 reveals, the upper and lower legs are adapted to grip the cutter bar receiving structure 34 of insert 14 when the cutter bar is installed thereon.

The foregoing description of the subassembly 18, including insert 14 and cutter bar 20, is offered to provided the reader with an appreciation of typical components which apparatus 10 is capable of assembling. Subassembly 18 and its component parts do not form part of the present invention. Neither, however, should the illustrated versions of the insert 14 and cutter bar 20 be construed as limitative of the sorts of parts that apparatus 10 is capable of assembling.

Turning again to FIG. 1, first conveyor 12 preferably comprises a generally horizontally extending variable speed endless belt type conveyor. The belt, identified by reference numeral 42, may be formed from any material having a coefficient of friction sufficient to propel the inserts 14 with minimal slippage. In this regard, a presently preferred belt material is urethane. To assure that the inserts maintain a uniform orientation during travel, conveyor 12 is also desirably provided with a pair of opposed parallel guide rails 44 and 46 which are adapted to closely receive the superstructure of the inserts, specifically platform 24 and opposed flanges 26 and 30. Most preferably, guide rails 44, 46 are upwardly pivotable along their outer edges so as to enable a user to easily free any stuck inserts or service the belt 42.

Apparatus 10 also comprises a second conveyor 54 extending substantially perpendicular to the first conveyor 12. The second conveyor transports cutter bars 20 from an unillustrated source of cutter bars in side-by-side serial relation to a second assembly station of assembly member 16. The second conveyor is preferably a rail-type conveyor inclined at an angle of approximately 10° to 20° with respect to horizontal which is gently vibrated by a suitable vibrator (not illustrated) to facilitate sliding of the cutter bars down the rail. The synchronous operation of the first and second conveyors 12, 54, the assembly member 16 and other features of the present invention will be more fully appreciated by reference to the discussion of FIG. 3, infra.

Referring to FIG. 2, apparatus 10 is shown to further comprise means for moving the assembly member 16 into a plurality of positions which correspond to a plurality of assembly stations of the apparatus. Assembly member 16 preferably is constructed as a generally vertically disposed, rotatable wheel or disk having a substantially horizontal axis of rotation. Apparatus 10 further includes drive means contained within a housing 56 for rotating the wheel 16 between the several assembly stations. The drive means must be capable of intermittently rotating the wheel through precise angles of arc in order to accurately position the assembly member at the designated assembly stations. A presently preferred embodiment of the drive means includes a brushless servo motor 58 connected to a right angle planetary gear head 60. The gear head 60 is operably connected to a first end of a shaft 62, preferably via a flexible coupling 64. Shaft 62, in turn, is rotatably supported by bearings 66 provided in support members 68 and 70. The opposite end of shaft 62 is fixedly and drivingly connected to wheel 16 via a key 72, a retainer plate 74 and a locking bolt 76.

As can be seen in each of FIGS. 2 and 3, apparatus 10 preferably includes an insert guide means 78, discussed hereinbelow, which is connected to an upper portion of support member 70. Projecting from a central portion of the guide means 78 is an L-shaped stop block 80 which permits passage of the second web 32 and cutter bar receiving structure 34 of the insert 14 as the wheel 16 is rotated. The downwardly depending leg of stop block 80 supports a small permanent magnet 82 whose function is described below in connection with FIG. 3.

The assembly wheel 16 has at least one or, more preferably, a plurality of unobstructed, open-faced holding slots or pockets 84 adapted to securely yet gently receive inserts delivered from the first conveyor 12. According to the presently preferred embodiment, wheel 16 includes eight such pockets radially disposed about its periphery and equiangularly spaced by 45° angles. Pockets 84 are preferably configured to cooperate with inserts having the general shape of the insert 14 shown in FIG. 4. In particular, pockets 84 are desirably formed to have an enlarged radially inwardly disposed portion 86 of a size sufficient to accommodate the dental floss spool arbor 22 of an insert. In addition, each pocket preferably includes a ledge 88 adapted to support the undersurface of an insert platform 24. Wheel 16 also desirably includes an enlarged diameter backing plate 90 which defines an abutment surface 92 for the first insert web 28 as well as a support surface 94 for the first insert flange 26 (see FIGS. 1 and 2).

As presently contemplated, the guide means 78 includes an elongated, generally semi-circular rail 78a which, as shown in FIG. 2, projects downwardly into and substantially mates with the space in the insert superstructure defined between the first web 28, the second web 32 and the upper surface of the platform 24. Rail 78a functions to positively urge the insert into seated and stable contact with its associated wheel pocket 84 as the wheel travels from the first to the third assembly stations described below. More particularly, the guide rail 78a is adapted to lightly contact the superstructure of insert 14 as the insert traverses the guide means 78 such that the undersurface of the platform remains in abutting relation with the ledge 88 while the first insert web 28 and first insert flange 26 maintain abutment with the abutment surface 92 and support surface 94, respectively, of the wheel backing plate 90. The stability thus afforded by the guide means 78 assures that the insert is processed and inspected with a high degree of precision as it progress through the assembly stations of apparatus 10. Such precision, in turn, translates into fewer misassembled cutter bar/insert subassemblies, thereby further enhancing the efficiency of the assembly apparatus.

Figure 3:
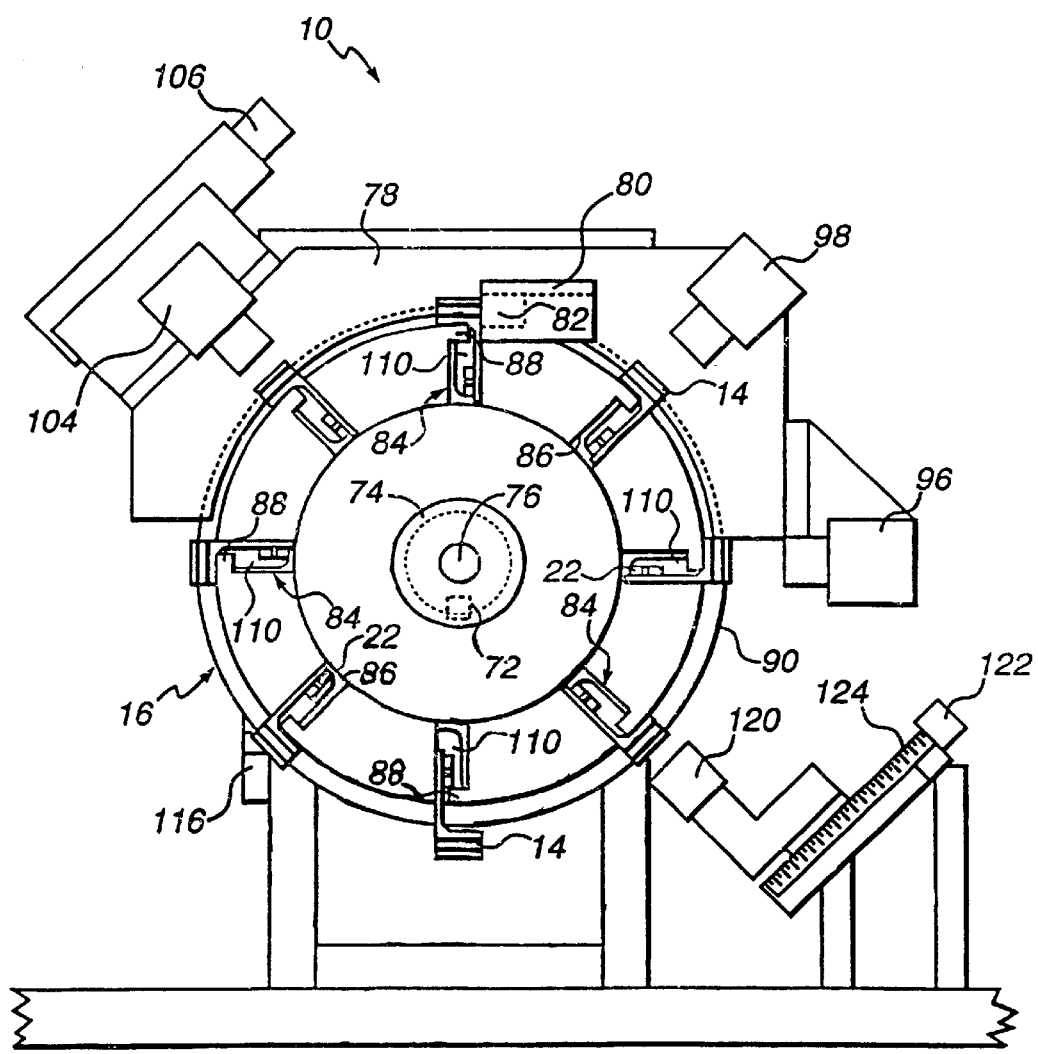
FIG. 3 is a front elevation view of the assembly member of the cutter bar/insert assembly apparatus of the present invention.

The first assembly station of apparatus 10 is that corresponding to the three o'clock position of wheel 16 as depicted in FIG. 3. Although not shown in that figure, the first conveyor 12 is precisely aligned with the first assembly station. As such, when an empty holding pocket 74 arrives at the first assembly station, the first conveyor delivers the leading insert into the holding pocket in the direction of the "IN" arrow shown in FIG. 1. The insert thus comes to rest against abutment surface 92 and is supported by ledge 88 and support surface 94. Upon installation of an insert into a pocket at the first assembly station, a first sensing means 96 such as a photoelectric sensor or the like transmits a signal to an unillustrated automatic apparatus control system such as a computer. The computer, in turn, processes the "insert present" signal from sensing means 96 and generates and transmits a motor control signal causing motor 58 to rotate the wheel 16 through an arc of approximately 45° in a counterclockwise direction (when viewing the wheel from the perspective shown in FIG. 3). In addition to sensing means 96 and motor 58 the computer responds to and/or synchronously controls several other mechanisms to be described hereinafter.

At this stage, the insert is inspected by another suitable sensing means 98 (which again may be a photoelectric sensor or the like that may for convenience be attached to the guide means 78). The function of sensing means 98 is to determine whether an insert is properly inserted in a pocket 84. If the computer receives a signal from the sensing means indicating a properly positioned insert, the computer logic generates and transmits a control signal to motor 58 causing same to index the wheel 16 through another 45° arc such that the insert arrives at a second assembly station corresponding to the twelve o'clock position of the wheel.

As shown in FIGS. 1 and 2, the stop block 80 and its associated magnet 82 are spaced from the discharge end of the second conveyor 54 a distance slightly greater than the width of a cutter bar 18. The magnetic attractive force of magnet 82 is sufficient to draw the leading cutter bar from the second conveyor and hold the cutter bar edgewise against the stop block. Simultaneously, the lower leg 40 of the magnetically suspended cutter bar 20 is supported on the upper surface of a substantially horizontal extension of a generally elongated push tool 100. The push tool is a component of a presently preferred means for placing a cutter bar onto the insert's cutter bar receiving structure 34. Such placement means also preferably comprise an extendable and retractable linear operator means 102 such as a pneumatic piston and cylinder or similar assembly connected to an appropriate source of pressurized air and valving. A linear operator is preferable because it avoids misalignment problems of the cutter bar 18 versus the cutter bar receiving structure 34 that often occurs with cam-driven cutter bar placement members.

If the presence of a waiting insert is detected at the second assembly station, the computer logic generates and transmits a control signal to the operator means 102 causing the piston thereof carrying the push tool 100 to extend toward the insert and thereby force the open mouth of suspended cutter bar 18 onto the cutter bar receiving structure. Upon placement of the cutter bar, the piston of the linear operator means is retracted to a ready position whereby another cutter bar is stripped from the second conveyor 54 by magnet 82 to await placement upon a subsequent insert. The surface of the stop bar 80 facing the second conveyor serves to maintain lateral alignment of a cutter bar as it approaches an insert during extension of the linear operator means 102. Similarly, the push tool 100 acts as a positive gate preventing the inadvertent discharge of additional cutter bars during the active phase of the linear operator means.

Referring again to FIG. 3, following completion of the cutter bar attachment operation, the computer logic commands the motor 58 to rotate wheel 18 another counterclockwise 45° arc. At this location, another sensing means 104 which, like sensing means 96 and 98, may assume the form of a photoelectric sensor or similar means attached to guide means 78. In addition, adjustment of the sensing means 104, as well as any of the sensing means previously or subsequently described, may be achieved via an adjustment mechanism such as, for example, a manually operated knob 106 connected to a threaded shaft.

Sensing means 104 inspects the relative positions of the cutter bar 20 and insert 14 of the assembled cutter bar/insert subassembly 18 to determine whether the cutter bar is properly installed on the insert. Depending on the condition detected, the sensing means 104 transmits a signal to the computer indicating either that the subassembly is properly assembled and, therefore, constitutes a "good" part, or that the subassembly is improperly assembled or otherwise defective, thereby constituting a "bad" or reject part. Upon receipt of either the "good" or "bad" part signal from sensing means 104, the computer directs the drive motor to rotatably index the wheel 16 in a counterclockwise direction to either one of two third assembly stations.

More specifically, sensing means 104 may indicate that the subassembly 18 is a good part. In that case, the computer would cause the motor 58 to rotate the wheel 45° counterclockwise, i.e., to the nine o'clock position. As shown in FIG. 3, the rail 78a of insert guide means 78 preferably terminates slightly above the nine o'clock position of wheel 16 whereby the subassembly is released from engagement with the rail 78a that would otherwise hinder its discharge from its respective wheel pocket. Referring to FIG. 1, it will be seen that adjacent the nine o'clock position of wheel 16 there is mounted to the housing a means 108 for discharging the subassembly 18 from its associated wheel pocket 84. Although any mechanical or electromechanical means may be used for this purpose, it has been discovered that the subassembly may be effectively discharged from its associated pocket 84 by a pulse of pressurized air. To that end, the backing plate 90 of wheel 16 is provided with a plurality of openings 110 associated with each of the pockets 84. And, discharging means 108 preferably comprises a simple block 112 having an air delivery passageway 114 connected at one end to an unillustrated source of pressurized air (e.g., the same pressurized air source used to supply the aforesaid linear operator means 102). The opposite end of the air passageway 114 defines an outlet directed toward the insert 14.

At the moment a "good" subassembly 18 arrives at the nine o'clock position of wheel 16, the computer logic generates and transmits a suitable control signal to the unillustrated pneumatic system thereby causing a pulse of pressurized air to be released from the air passageway 100. The pulse of air passes through the appropriately aligned wheel backing plate opening 110 to positively eject the subassembly 18 from its associated wheel pocket in the direction of the "OUT" arrow shown in FIG. 1. Because the subassembly is discharged from the open-faced assembly wheel pocket in a direction opposite its direction of insertion and also because, unlike certain prior art systems wherein the receiving pockets have obstructive gripping means which resist ready dislodgment of the subassemblies, a subassembly is in virtually all cases easily and completely discharged from the assembly wheel 16 through operation of means 108. When ejected from its wheel pocket 84 the good subassembly 18 passes through an unillustrated chute to a collecting bin for later assembly into a dental floss dispenser case.

If, however, sensing means 104 determines that a subassembly constitutes a bad or defective part, the computer would cause the motor 58 to rotate the wheel 90° to a position intermediate the nine o'clock and six o'clock positions. When a "bad" subassembly reaches this point, a discharge means 116 (partially shown in FIG. 3) substantially similar in construction and function to discharge means 108 is activated by the computer to eject the subassembly through a different unillustrated chute whereupon it may be captured in a different collecting bin from which it may be recovered and visually inspected.

Following discharge of a subassembly, and regardless of whether a subassembly has been judged good or bad, the computer logic operates the motor 58 to rotate the wheel 16 counterclockwise from the respective good or bad part discharge site of the third assembly station to the six o'clock position. FIG. 2 reveals that apparatus 10 further comprises a sensing means 118 disposed at this site to determine whether a subassembly has been successfully discharged from either the good or bad part ejection sites. Sensing means 118 preferably comprises a through-beam optical sensor. And, for purposes of illustration, a subassembly is shown in FIGS. 1 and 3 which has not been fully discharged from wheel 16. Note that at the six o'clock position the undischarged subassembly falls by gravity until its arbor 22 contacts the underside of ledge 88 and its superstructure interrupts the beam generated by sensing means 118. If such a condition is detected, the computer suspends operation of the motor 58. The person operating the apparatus may then physically remove the jammed part and then restart the assembly process.

In the event the subassembly has been successfully discharged, sensing means 116 transmits a signal reflecting this condition to the computer. The computer, in turn, causes the motor to rotate the wheel 16 an additional 45° counter-clockwise arc to a "home" position. At this position there is preferably located another sensing means 120 which is used to calibrate the assembly member 16. Calibration typically occurs prior to an assembly production run and recalibration is only occasionally necessary. An adjustment knob 122 similar to knob 106 of sensing means 104 may be used to turn a threaded shaft 124 to effectuate proper calibration of a home sensing means 120. The home sensing means may also assume the form of a photoelectric or similar sensor.

The provision of a home sensing means in cooperation with a servo motor represents an improvement over the prior art in that such a system indexes the assembly wheel responsive to the presence of an insert rather than to specifically prescribed stations. In prior systems, the indexing motors were designed to rotate the assembly member through preset angles of rotation. As a consequence, in known assembly apparatus frequent recalibration is common. In accordance with the present invention, however, the home sensing means 118 and motor 58, under control of the computer, afford a measure of ongoing self-compensation which allows the apparatus to function effectively for long periods of time. Furthermore, the foregoing description has discussed the operation of the apparatus 10 with respect to an individual insert at sequential stages of an assembly process. It will be understood, however, that such procedures may occur simultaneously upon several inserts under the direction of the computer logic when assembly member 16 is a multi-pocketed wheel or similar device whereby several subassemblies 18 may be concurrently and synchronously assembled. In addition, the computer logic permits rotation of the assembly wheel 16 only when all inspection and jam sensor conditions are satisfied.

If home sensing means 120 determines that the apparatus is properly calibrated it sends an "OK" signal to the computer. The computer then generates and transmits a control signal which causes the motor 58 to rotate the wheel an additional 45° counterclockwise arc whereby the empty pocket returns to the first assembly station to receive a new insert 14 from conveyor 12. The assembly process is thus repeated indefinitely until a condition such as jamming, an undischarged subassembly, necessary system recalibration, and the like, is detected.

The present invention thus provides a system including an apparatus and method which enables gentle, reliable and rapid assembly of the cutter bar/insert subassembly of a dental floss dispenser which minimizes the likelihood of part jams and other inherent deficiencies prevalent in related assembly systems presently known in the art. By doing so, such subassemblies may be produced at greater speeds and at lower cost than existing systems will permit.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Apparatus for assembling a cutter bar and an insert into a subassembly for use in a dispenser for thread products, said cutter bar including a cutting blade portion and said insert including a body portion defining an arbor adapted to rotatably support a spool of wound thread and a superstructure contiguous with said body portion, said superstructure including a platform, a first flange joined by a first web to said platform, a second flange joined by a second web to said platform and cutter bar receiving structure carried by said second flange, said apparatus comprising:

a assembly member including at least one pocket;

means for moving said assembly member into a plurality of positions corresponding to a plurality of assembly stations of said apparatus;

means for inserting an insert in a first direction into said at least one pocket at a first of said assembly stations;

means for delivering a cutter bar to a second of said assembly stations;

operator means for connecting a cutter bar to the cutter bar receiving structure of an insert at said second assembly station; and discharge means for discharging at least an insert from said at least one pocket in a direction substantially opposite said first direction at a third of said assembly stations.

2. The apparatus of claim 1 wherein said means for inserting a cutter bar comprise a first conveyor for delivering inserts from a source of inserts to said first assembly station.

3. The apparatus of claim 2 wherein said means for delivering a cutter bar comprise a second conveyor for delivering cutter bars from a source of cutter bars to said second assembly station.

4. The apparatus of claim 1 wherein said assembly member includes a backing plate and said at least one pocket includes an enlarged receiving portion and a ledge, said backing plate defining an abutment surface for the first web of an insert and a support surface for the first flange of an insert, and said ledge defining a support surface for the platform of an insert.

5. The apparatus of claim 1 wherein said assembly member comprises a plurality of pockets.

6. The apparatus of claim 1 wherein said assembly member comprises a rotatable wheel and said means for moving said assembly member comprises means for rotating said wheel.

7. The apparatus of claim 6 wherein said means for rotating said wheel comprise a servo motor.

8. The apparatus of claim 6 wherein said wheel is generally vertically disposed and has a substantially horizontal axis of rotation.

9. The apparatus of claim 1 wherein said discharge means comprise first means for discharging a properly connected insert and cutter bar from said at least one pocket.

10. The apparatus of claim 9 wherein said discharge means further comprise second means for discharging either an insert or an improperly connected insert and cutter bar from said at least one pocket.

11. The apparatus of claim 1 wherein said discharge means comprise means for directing a pulse of pressurized air toward an insert received in said at least one pocket.

12. The apparatus of claim 1 further comprising means disposed between said first and second assembly stations for determining whether an insert is properly inserted in said at least one pocket.

13. The apparatus of claim 1 further comprising means disposed between said second and third assembly stations for determining whether a cutter bar is properly connected to an insert.

14. The apparatus of claim 1 further comprising means disposed between said third assembly station and said first assembly station for determining whether an insert has been discharged from said at least one pocket.

15. The apparatus of claim 1 wherein said operator means comprise an extendable and retractable linear operator.

16. The apparatus of claim 15 wherein said extendable and retractable linear operator is a piston and cylinder assembly.

17. The apparatus of claim 16 wherein said operator means further comprise a push tool connected to a piston of said piston and cylinder assembly for pushing a cutter bar onto the cutter bar receiving structure of an insert.

18. The apparatus of claim 17 further comprising a stop block and means carried by said stop block for suspending a leading cutter bar delivered by said means for delivering a cutter bar at a location adjacent said second assembly station.

19. The apparatus of claim 18 wherein said stop block defines a surface for maintaining alignment of a cutter bar as the cutter bar is pushed onto the cutter bar receiving structure of an insert.

20. The apparatus of claim 19 wherein said means for suspending a leading cutter bar is a magnet.

21. The apparatus of claim 1 further comprising means for urging an insert into seating contact with said at least one pocket as said assembly member moves between said assembly stations.

* * * * *